United States Patent [19]

Vogt et al.

[11] 4,387,263

[45] Jun. 7, 1983

[54] PROCESS FOR MIXING OLEFINS

[75] Inventors: Wilhelm Vogt, Hürth; Hermann Glaser, Erftstadt; Jürgen Koch, Brühl, all of Fed. Rep. of Germany

[73] Assignee: Hoechst Aktiengesellschaft, Fed. Rep. of Germany

[21] Appl. No.: 378,425

[22] Filed: May 14, 1982

[51] Int. Cl.³ .............................................. C07C 1/24
[52] U.S. Cl. ..................................... 585/640; 585/639
[58] Field of Search ........................ 585/639, 638, 640

[56] References Cited

U.S. PATENT DOCUMENTS

| 2,236,535 | 4/1941 | Hasche | 585/638 |
|---|---|---|---|
| 2,435,038 | 1/1948 | Gilbert et al. | 585/640 |
| 2,542,488 | 2/1951 | Dinwiddie | 585/640 |
| 2,949,493 | 8/1960 | Happel et al. | 585/640 |
| 3,217,055 | 11/1965 | Edwards et al. | 585/639 |
| 3,894,107 | 7/1975 | Butter et al. | 585/640 |
| 4,036,905 | 7/1977 | Kornfield | 585/639 |
| 4,049,573 | 9/1977 | Kaeding | 585/640 |
| 4,052,479 | 10/1977 | Chang et al. | 585/640 |
| 4,060,568 | 11/1977 | Rodewala | 585/640 |
| 4,062,905 | 12/1977 | Chang et al. | 585/640 |

*Primary Examiner*—Delbert E. Gantz
*Assistant Examiner*—Cynthia A. Prezlock

*Attorney, Agent, or Firm*—Connolly and Hutz

[57] ABSTRACT

The disclosure relates to a process for making $C_2$ to $C_4$-olefins from gas mixtures containing methanol, dimethylether and optionally steam in the presence of catalysts at temperatures of 250° to 500° C. under pressure of 0.1 to 6 bars, unreacted feed material being recycled. To this end, the disclosure provides for a mixture containing methanol and water in a ratio by volume of 1:(0 up to 2) to be evaporated and reacted in a reactor having the catalyst placed therein; for the reaction gases to be partially condensed by cooling them and separated, in a separator, into three phases; for the oil phase consisting of higher aliphates and aromates to be removed and for the remaining aqueous phase and gas phase to be water-scrubbed in a scrubbing column under pressures of 1 to 40 bars; for a gaseous hydrocarbon mixture containing predominantly $C_2$ to $C_4$-olefins to be removed overhead and separated into its components; for an aqueous phase containing unreacted methanol and intermediarily formed dimethylether to be removed from the base portion of the scrubbing column; for the methanol and dimethylether to be distilled off in a stripping column and recycled into the reactor; and for the water to be removed from the base portion of the stripping column.

11 Claims, 1 Drawing Figure

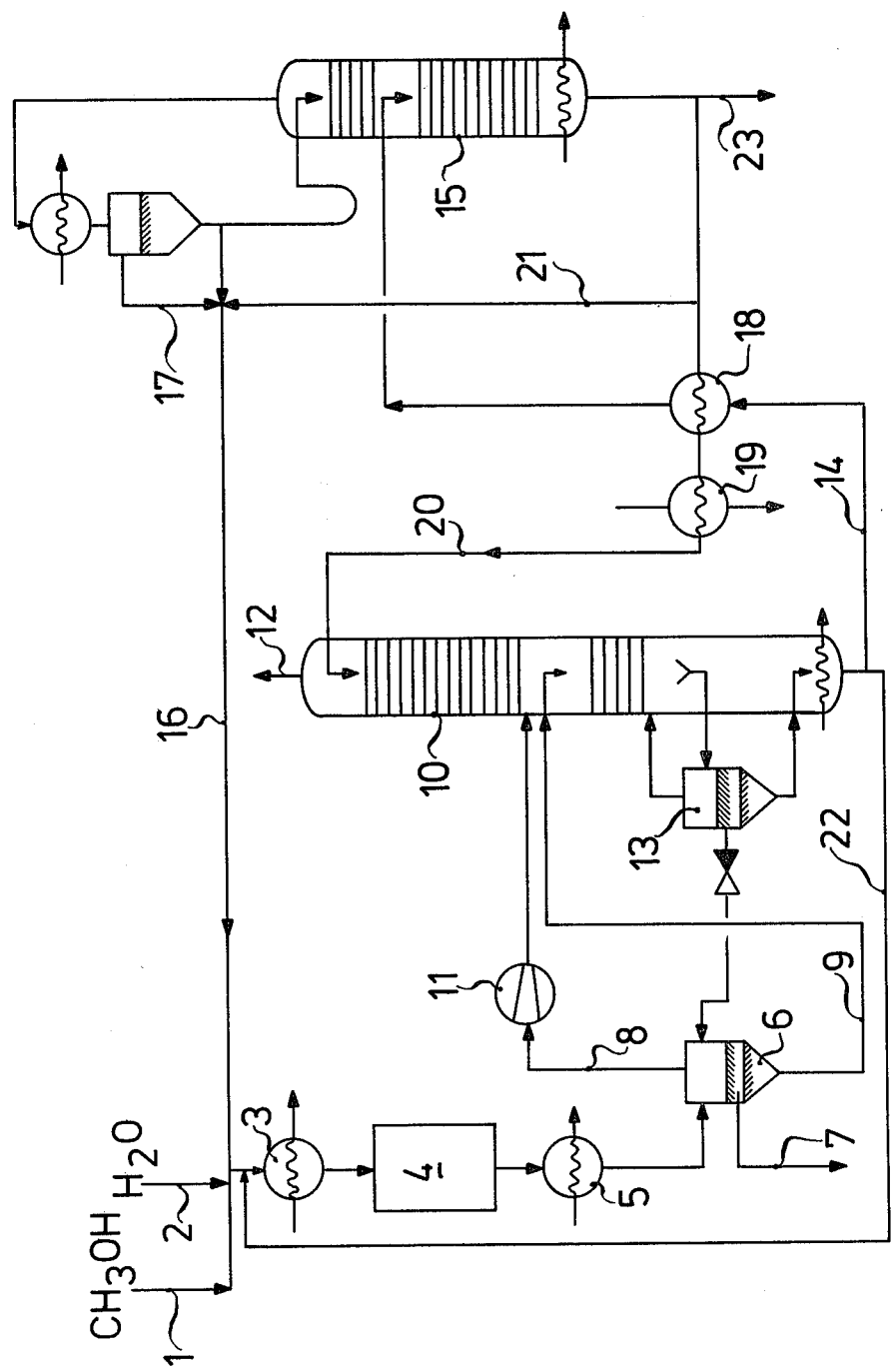

PROCESS FOR MIXING OLEFINS

The present invention relates to a process for making $C_2$ to $C_4$-olefins from gas mixtures containing methanol, dimethylether and optionally steam in the presence of catalysts at temperatures of 250° to 500° C. under pressures of 0.1 to 6 bars, unreacted feed material being recycled.

A process of this kind has already been described in U.S. Pat. No. 4,052,479, which is carried out at very high liquid hourly space velocities (briefly LHSV hereinafter) within the range 50 to 1000 liters liquid methanol and dimethylether per liter of catalyst per hour, in an attempt to reduce the feed material conversion rate to 5 to 25%.

A similar process wherein a feed mixture free from water is used has been described in U.S. Pat. No. 4,062,905, wherein the LHSV is as low as 0.1 to 200, and preferably 1 to 20.

In these two earlier processes use is made of catalysts which are selected from different types of zeolites, preferably however from H ZSM-5 type zeolites. Concerned are more particularly zeolites which commonly have a $SiO_2: Al_2O_3$-ratio of 10–60 and are made with the aid of a $SiO_2$- or $Al_2O_3$-gel as a strengthening agent into granular catalysts (particles with a size of 3 to 6 mm) for use in fixed bed reactors, or into pulverulent catalysts (particles with a size of 30 to 150 microns) for use in fluidized bed reactors. These statements are also true concerning the process of this invention.

No process has however been described heretofore which would permit the reaction products to be worked up in satisfactory manner. Only a two-stage process has been described in 1977 by Park L. Morse in Report No. 111, Process Economics Program, SRI, Menlo Park, Calif., "Methanol as a chemical raw material", wherein methanol is split, in a first reactor, into dimethylether and steam, and dimethylether in turn is split, in a second reactor, into ethylene and steam.

The present process now comprises: evaporating a mixture containing methanol and water in a ratio by volume of 1:(0 up to 2) and reacting it in a reactor having the catalyst placed therein; partially condensing the reaction gases by cooling them and separating them, in a separator, into three phases; removing the oil phase consisting of higher aliphates and aromates and water-scrubbing the remaining aqueous phase and gas phase in a scrubbing column under pressures of 1 to 40 bars; removing overhead a gaseous hydrocarbon mixture containing predominantly $C_2$ to $C_4$-olefins and separating it into its components in known manner; removing, from the base portion of the scrubbing column, an aqueous phase containing unreacted methanol and intermediarily formed dimethylether; distilling off therefrom in a stripping column, the methanol and dimethylether and recycling them into the reactor; and removing the water from the base portion of the stripping column.

Further preferred features of the present process provide:

(a) for the catalyst to contain a H ZSM-5 type zeolite and for the reaction to be carried out under pressures of 0.1 to 3 bars and at temperatures increasing from 280° to 360° C., the temperature being increased consistently with the gradually decreasing catalyst activity;

(b) for the reaction temperature to be controlled so as to ensure the conversion of an at most 80% proportion of methanol to hydrocarbons, during each passage;

(c) for the scrubbing column to comprise an upper absorption zone, a lower expelling zone and an oil separator for hydrocarbons condensing out;

(d) for 1 liter scrubbing water to be used in the scrubbing column per 3 to 200 normal liters gaseous hydrocarbon mixture which is removed overhead;

(e) for the temperature in the base portion of the scrubbing column to be by 5° to 40° C. higher than the temperature in the column head;

(f) for a portion of the scrubbing solution removed from the base of the scrubbing column to be evaporated and recycled into the reactor;

(g) for the stripping zone to be operated at the boiling temperature of water;

(h) for a quantity of water which corresponds at least to the reaction water formed during each passage to be removed from the system, the said quantity being taken from the water removed from the base portion of the stripping column;

(i) for a portion of the water removed from the base of the stripping column to be cooled and recycled to the head of the scrubbing column;

(j) for a portion of the water removed from the base of the stripping column to be recycled to the reactor for diluting the methanol therein.

The reaction of this invention can be carried out by flowing methanol in vapor form at liquid hourly space velocities (LHSV) of 0.1 to 10 liters liquid methanol per liter catalyst per hour over the catalyst, which should have a temperature within the range 250° to 500° C., the temperature being selected in accordance with the initial catalytic activity and loss of catalytic activity during operation. A narrower temperature range which should preferably be maintained for a H ZSM-5 type catalyst should commence at 280° C. for the fresh catalyst and end at 360° C. after gradual loss of catalytic activity inasmuch as any compensation for loss of catalytic activity by increasing the temperature beyond 360° C. increases the undesirable content of higher (from $C_5$ onward), especially aromatic hydrocarbons in the reaction product-mixture containing aliphatic compounds together with benzene, toluene, and isomers of xylene, tri- and tetramethylbenzenes.

Increasing the reaction pressure is in conflict with the goal of this invention, namely to produce reaction product containing lower olefins ($C_2$ to $C_4$) in the highest proportion possible. While it is basically possible for the methanol to be split under pressures higher than 10 bars, it is good practice to operate the reactor under a pressure of at most 6 bars, preferably 3 bars, in view of the goal aforesaid.

By the addition of water to methanol in a ratio by volume of (0.1–2):1, it is possible to favor the formation of lower olefins and reduce the formation of higher hydrocarbons.

These conditions respected, the yield of lower olefins is additionally and considerably determined by the methanol conversion rate, as results from the following Table:

| Conversion of $CH_3OH$ to hydrocarbons general in % | $C_2$ | $C_3$ | Oil |
|---|---|---|---|
| | (mol % C, based on C used) | | |
| 90 | 24.7 | 11.8 | 28.9 |
| 81 | 29.9 | 15.5 | 22.3 |
| 69 | 31.6 | 18.2 | 19.3 |
| 59 | 31.8 | 20.2 | 17.3 |
| 51 | 33.8 | 22.2 | 15.6 |

| Conversion of CH3OH to hydrocarbons general in % | C2 | C3 | Oil |
|---|---|---|---|
| | (mol % C, based on C used) | | |
| 44 | 34.0 | 22.8 | 11.9 |

It is therefore reasonable to limit the methanol conversion to hydrocarbons to ≦80%, a portion of the methanol not converted to hydrocarbons undergoing reaction to the dimethylether intermediary stage.

In the present process, it is critically important that methanol not converted to hydrocarbons during a single passage through the reactor, and dimethylether should be circulated and in this manner reacted completely. This condition must be met by a commercially attractive process.

Unreacted methanol and dimethylether should preferably be recycled through a scrubbing column having a stripping column placed downstream thereof; the scrubbing column can incidentally be operated under a pressure the same as that selected for operating the reactor; to reduce the quantity of scrubbing water to be used, it is more economic however by means of a compressor disposed between the reactor and scrubbing column, to increase the operating pressure to up to 40 bars, preferably 20 bars, inasmuch as it is anyway necessary for the olefinic hydrocarbon gas produced to be worked up under elevated pressure in a series-connected separating unit which however does not form part of the invention.

The process of this invention will now be described with reference to the accompanying drawing, in which conveying means, except for compressor 11, are not shown.

Methanol and water in the ratio of 1:(0-2) travelling through lines 1 and 2, respectively, are introduced into reactor 4 via evaporator 3. Reactor 4 is either a fixed bed reactor, which is packed with zeolite-catalyst, or a fluidized bed reactor which is provided with a separating unit to avoid the ejection of dusty material. The gaseous reaction product comprised of a wide variety of aliphatic and aromatic hydrocarbons and also of unreacted methanol and dimethylether is partially liquefied at about 25° C. in condenser 5 and separated in separator 6 into an aqueous phase, oil phase and gas phase, of which the oil phase formed of higher aliphatic and aromatic hydrocarbons is a good power fuel (gasoline). It is removed at 7, whereas the aqueous phase and gas phase are introduced through lines 8 and 9, respectively, into scrubbing column 10. By means of compressor 11, it is possible for the gas stream to be maintained under a pressure of up to 40 bars which incidentally is the pressure maintained in scrubbing column 10. This latter comprises an (upper) absorption zone with e.g. 20 bubble trays, and a (lower) expelling zone. The absorption zone is fed with 1 liter scrubbing water having a temperature e.g. of 20° to 40° C. per 3 to 200 liters product gas issuing through line 12 (120-200 l at 40 bars; 60-100 l at 20 bars; 3-5 l at 1 bar), the gas liters being in each case determined under standard conditions (1.013 bar and 273.15K). After having been dried, the gas is subjected to low temperature liquefaction, which does not form part of this invention.

The scrubbing water enables methanol and dimethylether to be dissolved and removed from the gas stream; hydrocarbons are also dissolved to some minor extent so that it is good practice for them to be expelled in the expelling zone of column 10 by means of dimethylether flowing countercurrently with respect thereto, the base portion of the scrubbing column being heated to 30° to 60° C., for example.

The temperature in the base portion should always be by 5° to 40° C. higher than the temperature in the head of scrubbing column 10 so that it is possible for the dimethylether to be partially expelled and travel upwardly in the expelling zone. As a result of the volume of the product gas quantity being reduced upon dissolution of the dimethylether portion in water, the gas stream becomes oversaturated with higher hydrocarbons which are partially precipitated as oil phase in the scrubbing column, removed through oil separator 13 and, if desired after pressure release, admitted to separator 6 and degassed therein. Scrubbing solution which is removed from the base of scrubbing column 10 is introduced through line 14 into stripping column 15 and freed therein from methanol and dimethylether, which are recycled partially in liquid form and partially in gaseous form into reactor 4, through lines 16 and 17, respectively. The pressure selected for operating stripping column 15 is variable so that it is possible for the pressure under which methanol and dimethylether are removed near the head of column 15 to be conformed to the pressure prevailing in the reactor inlet portion.

Water obtained in the base of stripping column 15 (temperature e.g. 103°-108° C.) is cooled by means of heat exchangers 18 and 19 and then partially recycled through line 20 into scrubbing column 10 for use as scrubbing water therein (temperature e.g. 20° to 40° C.) and partially recycled, if desired, through line 21 into reactor 4, line 2 permitting the addition of water to be stopped. The same goal, namely to take water needed in the reactor from the scrubbing water cycle, can alternately be achieved by operating stripping column 15 at a high head temperature, preferably higher than 90° C. This makes it possible for the head product flowing through lines 16 and 17 back to reactor 4 to carry along with it the quantity of water needed per hour in the reactor. An even simpler operation than just described provides for a portion of the scrubbing solution which is removed from the base of the scrubbing column 10 to be directly recycled through conduit 22 into evaporator 13. The quantity of water split off from methanol and dimethylether, respectively, during each passage is removed through line 23 so that the overall quantity of water inside the system remains constant.

Technically beneficial effects of the operation cycle just described reside in the fact that only one reactor is required to be used and in the fact that it is unnecessary for unreacted methanol and dimethylether to be reacted in a second reactor.

EXAMPLE 1

3 l/h methanol (=2377 g CH3OH) and 3 l/h water (ratio by volume=1:1) were pumped through inlet lines 1 and 2 into evaporator 3. The evaporated methanol/water-mixture was introduced with an initial temperature of 320° C. and under a pressure of 1.2 bars into reactor 4. This latter was a fixed bed reactor which was packed with 1 liter extruded material with a size of 3 mm, of which 80 weight % was a H ZSM-5 type zeolite and 20 weight % binder. The LHSV accordingly was 3. Reaction mixture which came from the reactor was condensed in condenser 5 downstream of the reactor, to about 25° C. and separated in separator 6 into an oil phase, aqueous phase and gas phase, of which the oil phase consisting of higher aliphatic and aromatic hydrocarbons was removed through line 7. The aqueous phase was pumped through line 9 into the expelling zone of scrubbing column 10, whilst the gaseous products were introduced under a pressure of 20 bars into scrubbing column 10 at a level below the absorption zone therein, through line 8 and with the aid of compressor 11. The head portion of scrubbing column 10 was supplied per hour with about 5 l water at 25° C. flowing through line 20 which was used for scrubbing the gas mixture and free it from methanol unreacted in reactor 4 and intermediarily formed dimethylether. About 417 l/hour (determined at 1.013 bar and 273.15K) gas mixture composed of (in volume %)

0.4% CO
3.7% $CH_4$
51.2% $C_2H_4$
31.5% $C_3H_6$
11.8% $C_4$-hydrocarbons
1.4% higher hydrocarbons were taken from the scrubbing column 10 through line 12. (Ignored in the above composition are the about 2.5 volume % steam present under the temperature and pressure conditions selected (partial pressure)). 363 g/h oil components collected from separator 6 and oil separator 13 were removed at 7. The temperature prevailing in the base portion of the expelling zone of scrubbing column 10 was 40° C. The 320° C. temperature selected for reactor 4 ensured conversion of 80% methanol to hydrocarbons during a single passage. Unreacted methanol (8%) and dimethylether which had formed (12%, based on methanol used) were introduced together with scrubbing water, through line 14, into stripping column 15, of which the base was heated to 104° C. 190 g/h methanol (through line 16) and 205 g/h (100 normal liters/h) gaseous dimethylether (through line 17) were recycled from the head of stripping column 15 to reactor 4, via evaporator 3. Under these conditions, liquid and gaseous reaction products were obtained in the following average proportions (C-%), based on methanol used:

0.1% CO
1.0% $CH_4$
26% ethylene
24% propylene
12% butylene
36.9% higher aliphatic and aromatic hydrocarbons The decreasing catalytic activity was compensated by increasing the temperature to 360° C. After 24 hours, the initial reactor was switched off and operation was continued on a second reactor having reactivated catalyst placed therein. At the same time, the inactivated catalyst was regenerated oxidatively.

EXAMPLE 2

The procedure was as in Example 1 with the following exceptions:

A temperature of 300° C. was maintained in reactor 4 whereby methanol conversion to hydrocarbons during a single passage was limited to 60%. 380 g/h methanol (through line 16) and 195 g/h gaseous dimethylether (through line 17) were recycled into reactor 4. 310 g/h oil phase was removed from separators 6 and 13, through line 7. 458 l/h (determined at 1.013 bar and 273.15K) gas mixture with the following composition (volume %) was obtained through line 12:

0.7% CO
3.1% $CH_4$
50.7% $C_2H_4$
31.3% $C_3H_6$
13.6% $C_4$-hydrocarbons the 2.5 volume % steam present under the temperature and pressure conditions prevailing (partial pressure) being ignored.

The yield of liquid and gaseous reaction products, based on methanol used was:

CO = 0.2 C-%
$CH_4$ = 1.0 C-%
$C_2H_4$ = 28.0 C-%
$C_3H_6$ = 25.9 C-%
$C_4H_8$ = 13.0 C-%
higher aliphatic and aromatic hydrocarbons = 31.5 C-%

EXAMPLE 3

3 liters methanol (=2377 g) and 3 liters water were passed at 320° C. over 1 liter catalyst under the conditions described in Example 1. The gaseous reaction products were cooled down to 25° C. in condenser 5, an oil phase and aqueous phase were separated in separator 6, and the remaining material was recycled without compression through line 9 into scrubbing column 10. 150 l/h water at 25° C. was pumped into the head of column 10 for freeing the reaction gas from unreacted methanol and dimethylether. To reduce the quantity of hydrocarbons dissolved in the scrubbing water, the base of column 10 was heated to 40° C. A gas mixture with the following composition was obtained at the head of scrubbing column 10 in an average quantity of 460 normal liters/h:

0.7 volume % CO
3.6 volume % $CH_4$
47.0 volume % $C_2H_4$
28.9 volume % $C_3H_6$
10.8 volume % $C_4H_8$
9.0 volume % higher hydrocarbons ($C_5$ to $C_8$)

the about 2.5 volume % steam present under the temperature and pressure conditions prevailing (partial pressure) being ignored. 214 g/h liquid products consisting essentially of benzene, toluene, xylenes and mesitylene were removed from separators 6 and 13. 190 g/h methanol (through line 16) and 205 g/h gaseous dimethylether (through line 17) were recycled into reactor 4. The methanol used gave in C-%:

0.2% CO
1.0% $CH_4$
26.0% $C_2H_4$
24.0% $C_3H_6$
12.0% $C_4H_8$
36.8% higher aliphatic and aromatic hydrocarbons

EXAMPLE 4

The conditions were as in Example 1. 3 liters methanol (=2377 g) but no water was passed at 320° C. over 1 liter catalyst. A gas mixture composed of 1.2 volume % CO
4.0 volume % $CH_4$
42.65 volume % $C_2H_4$
27.23 volume % $C_3H_6$
12.8 volume % $C_4H_8$
12.1 volume % higher hydrocarbons ($C_5$ to $C_8$)

was obtained in an average quantity of 415.5 normal liters per hour at the head of scrubbing column 10. 242 g/h liquid products consisting essentially of benzene, toluene, xylene and mesitylene were removed from separators 6 and 13. 170 g/h methanol (through line 16) and 185 g/h gaseous dimethylether (through line 17) were recycled into reactor 4. The methanol used gave in C-%:

0.3% CO
1.0% $CH_4$
21.3% $C_2H_4$
20.4% $C_3H_6$
12.8% $C_4H_8$
42.7% higher aliphatic and aromatic hydrocarbons

EXAMPLE 5

The procedure was as in Example 1, but the pressure in the scrubbing column was increased to 40 bars. 396 normal liters per hour of a gas consisting of:

0.42 volume % CO
4.2 volume % $CH_4$
54.63 volume % $C_2H_4$
31.93 volume % $C_3H_6$
8.82 volume % $C_4$-hydrocarbons was taken from scrubbing column 10, through line 12. Liquid products taken from oil separators 6 and 13 at 7 were obtained at a rate of 422 g/h. 3 liters water at 25° C. flowing through line 20 was introduced per hour into the head of scrubbing column 10.

We claim:

1. A process for making $C_2$ to $C_4$-olefins from gas mixtures containing methanol, dimethylether and optionally steam in the presence of catalysts at temperatures of 250° to 500° C. under pressure of 0.1 to 6 bars, unreacted feed material being recycled, which comprises: evaporating a mixture containing methanol and water in a ratio by volume of 1:(0 up to 2) and reacting it in a reaction zone having the catalyst placed therein; partially condensing the reaction gases by cooling them and separating them, in a separating zone, into three phases; removing the oil phase consisting of higher aliphatic and aromatic hydrocarbons and water-scrubbing the remaining aqueous phase and gas phase in a scrubbing zone under pressures of 1 to 40 bars; removing overhead a gaseous hydrocarbon mixture containing predominantly $C_2$ to $C_4$-olefins and separating it into its components; removing, from the base portion of the scrubbing zone, an aqueous phase containing unreacted methanol and intermediarily formed dimethylether; distilling off therefrom in a stripping zone, the methanol and dimethylether and recycling them into the reaction zone; and removing the water from the base portion of the stripping zone.

2. A process as claimed in claim 1, wherein the catalyst contains a H ZSM-5 type zeolite and the reaction is carried out under pressures of 0.1 to 3 bars and at temperatures increasing from 280° to 360° C., the temperature being increased consistently with the gradually decreasing catalyst activity.

3. A process as claimed in claim 1, wherein the reaction temperature is controlled so as to ensure the conversion of an at most 80% proportion of methanol to hydrocarbons, during each passage.

4. A process as claimed in claim 1, wherein the scrubbing zone comprises an upper absorption zone, a lower expelling zone and an oil separating zone for condensing hydrocarbons.

5. A process as claimed in claim 1, wherein 1 liter scrubbing water is used in the scrubbing zone per 3 to 200 normal liters gaseous hydrocarbon mixture removed overhead.

6. A process as claimed in claim 1, wherein the temperature in the base portion of the scrubbing zone is by 5° to 40° C. higher than the temperature in the head portion of said zone.

7. A process as claimed in claim 1, wherein a portion of the scrubbing solution removed from the base of the scrubbing zone is evaporated and recycled into the reaction zone.

8. A process as claimed in claim 1, wherein the stripping zone is operated at the boiling temperature of water.

9. A process as claimed in claim 1, wherein a quantity of water which corresponds at least to the reaction water formed during each passage is removed from the system, the said quantity being taken from the water removed from the base portion of the stripping zone.

10. A process as claimed in claim 1, wherein a portion of the water removed from the base of the stripping zone is cooled and recycled to the head of the scrubbing zone.

11. A process as claimed in claim 1, wherein a portion of the water removed from the base of the stripping zone is recycled to the reaction zone for diluting the methanol therein.

* * * * *